(12) United States Patent
Wenchell et al.

(10) Patent No.: US 8,070,731 B2
(45) Date of Patent: Dec. 6, 2011

(54) SURGICAL ACCESS APPARATUS

(75) Inventors: Thomas Wenchell, Durham, CT (US); Skott Greenhalgh, Wyndmoor, PA (US); David Farascioni, Bethel, CT (US)

(73) Assignee: Tyco Healthcare Group LP, North Haven, CT (US)

( * ) Notice: Subject to any disclaimer, the term of this patent is extended or adjusted under 35 U.S.C. 154(b) by 0 days.

(21) Appl. No.: 12/780,494

(22) Filed: May 14, 2010

(65) Prior Publication Data

US 2010/0222747 A1   Sep. 2, 2010

Related U.S. Application Data

(62) Division of application No. 10/830,522, filed on Apr. 23, 2004, now abandoned.

(60) Provisional application No. 60/540,421, filed on Jan. 30, 2004, provisional application No. 60/466,005, filed on Apr. 25, 2003.

(51) Int. Cl.
*A61M 5/178* (2006.01)

(52) U.S. Cl. .......... 604/167.06; 604/164.01; 604/167.01

(58) Field of Classification Search ............... 604/23, 604/26, 30, 34, 43, 44, 45, 167.03, 167.04, 604/167.06, 288.01, 288.02, 164.01, 167.01, 604/167.02, 288.03
See application file for complete search history.

(56) References Cited

U.S. PATENT DOCUMENTS

| | | | |
|---|---|---|---|
| 3,834,546 A | 9/1974 | Brun et al. |
| 4,447,237 A | 5/1984 | Frisch et al. |
| 4,540,411 A | 9/1985 | Bodicky |
| 4,655,752 A | 4/1987 | Honkanen et al. |
| 4,722,725 A | 2/1988 | Sawyer et al. |
| 4,909,798 A | 3/1990 | Fleischhacker et al. |
| 4,950,257 A | 8/1990 | Hibbs et al. |
| 4,978,341 A | 12/1990 | Niederhauser |
| 5,071,411 A | 12/1991 | Hillstead |
| 5,092,857 A | 3/1992 | Fleischhacker |
| 5,108,380 A | 4/1992 | Herlitze et al. |
| 5,127,626 A | 7/1992 | Hilal et al. |
| 5,147,336 A | 9/1992 | Wendell et al. |
| 5,158,553 A | 10/1992 | Berry et al. |
| 5,197,955 A | 3/1993 | Stephens et al. |
| 5,201,714 A | 4/1993 | Gentelia et al. |
| 5,209,736 A | 5/1993 | Stephens et al. |

(Continued)

FOREIGN PATENT DOCUMENTS

DE   37 37 121   5/1989

(Continued)

OTHER PUBLICATIONS

International Search Report from European Appln. No. EP 09 15 0425 dated Feb. 13, 2009 (2 pages).

(Continued)

*Primary Examiner* — Bhisma Mehta

(57) ABSTRACT

An access apparatus for use during a surgical procedure to provide access to the interior of the body includes an access member defining a longitudinal axis and having a proximal end for being disposed at an exterior side of the body and a distal end for extending into the interior of the body. The access member has a bore therethrough dimensioned to permit passage of an object. A seal is disposed within the bore of the access member. The seal includes a fabric material and an elastomeric material, and defines an internal passageway dimensioned to form a substantial sealing relation with an object inserted therethrough.

11 Claims, 9 Drawing Sheets

U.S. PATENT DOCUMENTS

| | | | |
|---|---|---|---|
| 5,209,737 | A | 5/1993 | Ritchart et al. |
| 5,242,412 | A | 9/1993 | Blake, III |
| 5,308,336 | A | 5/1994 | Hart et al. |
| 5,350,364 | A | 9/1994 | Stephens et al. |
| 5,360,417 | A | 11/1994 | Gravener et al. |
| 5,380,288 | A | 1/1995 | Hart et al. |
| 5,385,553 | A | 1/1995 | Hart et al. |
| 5,407,433 | A | 4/1995 | Loomas |
| 5,411,483 | A | 5/1995 | Loomas et al. |
| 5,431,676 | A | 7/1995 | Dubrul et al. |
| 5,476,475 | A | 12/1995 | Gadberry |
| 5,496,280 | A | 3/1996 | Vandenbroek et al. |
| 5,514,109 | A | 5/1996 | Mollenauer et al. |
| 5,545,142 | A | 8/1996 | Stephens et al. |
| 5,545,179 | A | 8/1996 | Williamson, IV |
| 5,584,850 | A | 12/1996 | Hart et al. |
| 5,634,911 | A | 6/1997 | Hermann et al. |
| 5,709,664 | A | 1/1998 | Vandenbroek et al. |
| 5,720,759 | A | 2/1998 | Green et al. |
| 5,752,970 | A | 5/1998 | Yoon |
| 5,792,113 | A | 8/1998 | Kramer et al. |
| 5,797,888 | A | 8/1998 | Yoon |
| 5,871,474 | A | 2/1999 | Thayer |
| 5,906,595 | A | 5/1999 | Powell et al. |
| 5,993,471 | A | 11/1999 | Riza et al. |
| 6,004,303 | A | 12/1999 | Peterson |
| 6,123,689 | A | 9/2000 | To et al. |
| 6,197,002 | B1 | 3/2001 | Peterson |
| 6,221,050 | B1 | 4/2001 | Ishida |
| 6,228,068 | B1 | 5/2001 | Yoon |
| 6,238,373 | B1 | 5/2001 | de la Torre et al. |
| 6,258,065 | B1 | 7/2001 | Dennis et al. |
| 6,276,661 | B1 | 8/2001 | Laird |
| 6,358,266 | B1 | 3/2002 | Bonutti |
| 6,447,489 | B1 | 9/2002 | Peterson |
| 6,482,181 | B1 | 11/2002 | Racenet et al. |
| 2001/0029353 | A1 | 10/2001 | Peterson |
| 2002/0128604 | A1* | 9/2002 | Nakajima ................ 604/164.01 |
| 2004/0044313 | A1* | 3/2004 | Nakajima ................ 604/167.02 |
| 2004/0059297 | A1 | 3/2004 | Racenet et al. |
| 2004/0162531 | A1* | 8/2004 | Wenchell ...................... 604/264 |
| 2004/0199121 | A1 | 10/2004 | Wenchell et al. |
| 2006/0149305 | A1 | 7/2006 | Cuevas et al. |
| 2008/0097332 | A1 | 4/2008 | Greenhalgh et al. |
| 2009/0105635 | A1 | 4/2009 | Bettuchi et al. |

FOREIGN PATENT DOCUMENTS

| | | |
|---|---|---|
| DE | 42 31 414 | 3/1994 |
| WO | 94/22357 | 10/1994 |
| WO | 98/53865 | 12/1998 |
| WO | 00/45720 | 8/2000 |

OTHER PUBLICATIONS

International Search Report from PCT/US04/13739 for the search Dec. 12, 2005 (1 pg).

Written Opinion of the International Searching Authority for PCT/US04/13739 dated Dec. 12, 2005 (3 pgs).

European Exam Report Application No. 04 751 227.2-2310 dated Sep. 24, 2010 (6 pgs).

The Canadian Search Report Application No. 2,522,617, dated Feb. 8, 2011, (5 pages).

Extended European Search Report from European Patent Application No. 11250370.1 mailed Jun. 29, 2011. 3 pages.

* cited by examiner

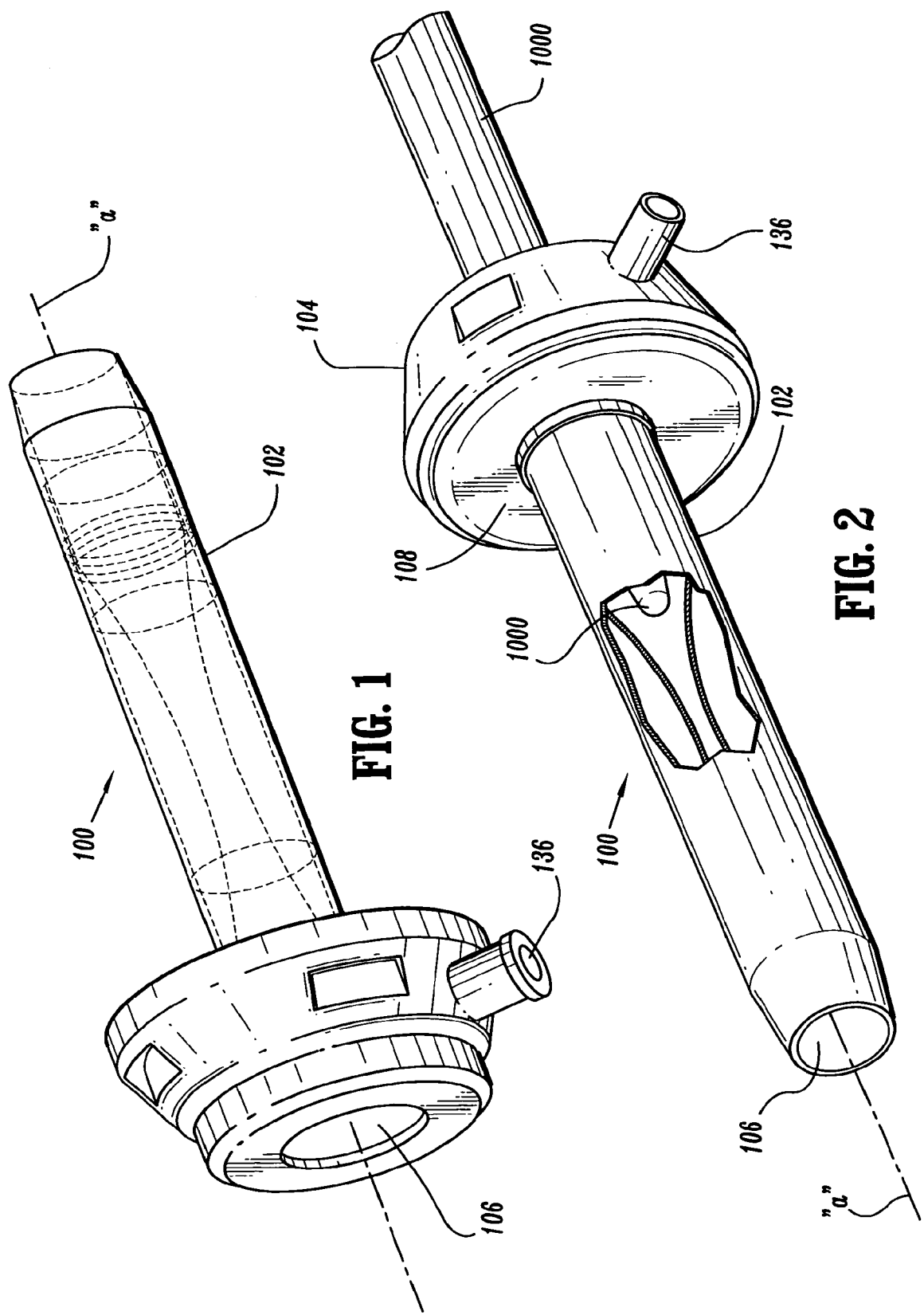

SURGICAL ACCESS APPARATUS

CROSS-REFERENCE TO RELATED APPLICATIONS

This application is a divisional of U.S. application Ser. No. 10/830,522, filed Apr. 23, 2004, published on Mar. 17, 2005 as U.S. Patent Application Publication No. 2005/0059934 A1, "SURGICAL ACCESS APPARATUS", and now abandoned, which claims priority to, and the benefit of, U.S. Provisional Application Ser. No. 60/540,421, filed Jan. 30, 2004 and U.S. Provisional Application Ser. No. 60/466,005, filed Apr. 25, 2003, the entire contents of which are incorporated herein by reference.

BACKGROUND

1. Field of the Disclosure

The present disclosure relates to surgical devices and, more particularly, to a surgical access apparatus for use during a minimally invasive surgical procedure. The present disclosure further relates to a novel seal assembly for forming a seal about a surgical object while accommodating angular manipulation of the surgical object.

2. Description of the Related Art

Minimally invasive surgical procedures including both endoscopic and laparoscopic procedures permit surgery to be performed on organs, tissues and vessels far removed from an opening within the tissue. Laparoscopic and endoscopic procedures generally require that any instrumentation inserted into the body be sealed, i.e. provisions must be made to ensure that gases do not enter or exit the body through the incision as, for example, in surgical procedures in which the surgical region is insufflated. These procedures typically employ surgical instruments which are introduced into the body through a cannula. The cannula has a housing at a proximal end thereof in which a seal assembly is mounted. The seal assembly provides a substantially fluid tight seal about the instrument to preserve the integrity of the established pneumoperitoneum. The housing extends above the patient's body, when the cannula is inserted into the incision, reducing the effective length of instruments inserted through the cannula and potentially encumbering maneuverability about the operative site.

Minimally invasive procedures have several advantages over traditional open surgery, including less patient trauma, reduced recovery time, reduced potential for infection, etc. . . . However, despite its recent success and overall acceptance as a preferred surgical technique, minimally invasive surgery, such as laparoscopy, has several disadvantages. In particular, the maintenance of the seal about the surgical instrument within the cannula has proven to be difficult in certain procedures, e.g., in procedures requiring extensive manipulation of the long narrow endoscopic instruments within a remote site. In addition, many conventional seal assemblies are not adapted to accommodate instruments of various sizes, while still maintaining the seal about the inserted instrument. Even further, known seal assemblies are relatively complex, which increases the length of the housing in which it is confined. As a consequence, maneuverability above the operative site and the effective length of the instrument are undesirably affected.

SUMMARY

Accordingly, the present disclosure is directed to an access apparatus for use during a surgical procedure to provide access to the interior of the body. The access apparatus includes an access member defining a longitudinal axis and having a proximal end for being disposed at an exterior side of the body and a distal end for extending into the interior of the body. The access member has a bore therethrough dimensioned to permit passage of an object. A seal is disposed within the bore of the access member. The seal includes a fabric material and an elastomeric material, and defines an internal passageway dimensioned to form a substantial sealing relation with an object inserted therethrough.

Preferably, the fabric material comprises a braided fabric material, and is generally elongated extending along the longitudinal axis of the access member. The braided fabric material may be a tubular braided fabric material.

The seal may include an outer surface with the elastomeric material being at least partially disposed at the outer surface. The outer surface is substantially impervious to passage of insufflation gases. The seal includes an inner surface with the braided fabric material being at least partially disposed at the inner surface for engagement with the instrument. The seal may be substantially impervious to passage of insufflation gases along a substantial length of the seal. Alternatively, the seal may include a porous section adjacent one end thereof to permit passage of insufflation gases.

The seal may be mounted within the access member to define an outer passageway between the seal and the access member. The seal may be secured to the access member at a first location along the longitudinal axis and may be secured to the access member at a second location along the longitudinal axis distal of the first location. The access member may include a channel extending distal of the first location for introduction of insufflation gases into the outer passageway. The porous section of the seal is adjacent the second location to permit passage of insufflation gases between the internal passageway of the seal and the outer passageway.

In one embodiment, the seal includes a constricted area which is expansible to engage the object in substantial fluid tight relation therewith. The elastomeric material is impregnated into the braided fabric material of the seal.

In another embodiment, the seal includes first and second ends. The first end of the seal is secured to the access member at a first location along the longitudinal axis. The second end of the seal is adapted for axial movement in response to passage of an object into the internal passageway of the seal. Preferably, the seal includes a seal mount which is adapted for longitudinal axial movement with the second end of the seal being secured to the seal mount.

In another embodiment, a cannula assembly for use in a surgical procedure is disclosed. The cannula assembly includes a cannula member defining a longitudinal axis and having a longitudinal bore therethrough for passage of a surgical instrument, a cannula housing defining an opening for receipt of the instrument with the cannula housing being connected to a proximal end of the cannula member so that the opening and the bore communicate with one another, and a sealing member mounted within the cannula member for forming a substantial seal with the instrument. The sealing member includes a fabric material which includes a plurality of strands and an elastomeric material.

The fabric material has an elongate shape extending along the longitudinal axis and a predetermined shape prior to insertion of the instrument. The fabric material has a proximal end, a distal end, and a sloped portion therebetween. The sloped portion defines a passageway for the receipt of the instrument and is arranged to form a substantial seal therewith. The fabric material comprises an expansible fabric and is arranged to expand upon engaging the instrument. The elastomeric material is disposed adjacent at least a center-portion of the sealing member. The center-portion is adapted to expand in receiving the instrument.

The fabric material may have a tubular shape and may be braided. The fabric material may include a plurality of monofilament strands and a plurality of multifilament strands.

The sealing member includes an outer surface with the elastomeric material being at least partially disposed at the outer surface. The outer surface is substantially impervious to passage of insufflation gases. The sealing member includes an inner surface with the fabric material being at least partially disposed at the inner surface, for engagement with the instrument. The elastomeric material may be impregnated into the fabric material of the sealing member.

The sealing member may include first and second ends with the first end being secured to the cannula member at a first location along the longitudinal axis. The second end is adapted for axial movement in response to the passage of an instrument through the sealing member. The cannula assembly may further include a seal mount adapted for longitudinal axial movement, whereby the second end of the sealing member is secured to the seal mount.

In another preferred embodiment, a surgical access apparatus for providing access to the interior of the body, includes an access member defining a longitudinal axis and having a proximal end for being disposed at an exterior side of the body and a distal end for extending into the interior of the body and a longitudinal passage extending therethrough, and an elongated seal coaxially mounted within the passage of the access member to define an outer passageway between the access member and the elongated seal. The seal includes a fabric material and an elastomeric material, and has a longitudinal passageway for receipt of an object therethrough in substantial sealed relation therewith. At least one of the access member and the elongated seal defines a port to permit communication of insufflation gases between the outer passageway and the longitudinal passage of the seal. The access member may include an insufflation port to permit passage of insufflation gases from an external source to the outer passageway, and may define a channel in communication with the insufflation port and the outer passageway.

The elongated seal includes an elastomeric material which is substantially impermeable to passage of insufflation gases. The elongated seal may have a distal end portion devoid of the elastomeric material to permit passage of insufflation gases through the fabric material between the outer passageway and the longitudinal passage of the seal.

The elongated seal may include an expansible fabric which is arranged to expand upon engaging the instrument. The sealing member may have a constricted shape for engaging the instrument at an area around a center of the elongated seal. The elongated seal may include an elastomeric material at least the center. The elongated seal may be secured to an inner surface of the access member at a first location along the longitudinal axis. The elongated seal may be secured to an inner surface of the access member at a second location disposed distally of the first location, so as to form the outer passageway between the elongated seal and the access member. The port is defined in the access member and disposed distally of the first location to allow the release of insufflation gases from the outer passageway.

The elongated seal may define a tubular shape. The elongated seal has a constricted shape defining the interior passageway of the elongated seal and being arranged so that upon insertion of the instrument through the interior passageway, the instrument expands the interior passageway forming a substantial seal therewith.

The access apparatus may also include a zero-closure seal mounted relative to the cannula member and adapted to close in the absence of the instrument.

In another alternative embodiment, the surgical access apparatus includes an access member defining a longitudinal axis and proximal and distal ends, and having a passageway therethrough dimensioned to permit passage of an object, and an elongated seal disposed within the passageway of the access member. The elongated seal includes a proximal end secured within the access member and a distal end mounted for axial movement within the access member. The distal end is moveable to a retracted position to permit the passageway of the elongated seal to expand to accommodate the object in substantial fluid tight relation therewith. Preferably, the elongated seal comprises a fabric and may be a tubular braided fabric. A seal mount may be attached to the distal end of the elongated seal and movable between extended and retracted positions.

In another preferred embodiment, a fabric material for a seal is disclosed. The fabric material includes a tubular braid of a plurality of strands having a polymeric material. Preferably, the tubular braid has between about 48 and about 196 strands which are selected from a group consisting of a plurality of monofilament strands having a diameter of between about 0.001 and about 0.007 inch, and a plurality of multifilament strands having a denier of between about 75 and about 300. The polymeric material is selected from the group consisting of polypropylene, nylon, Teflon, polyethylene terepthalate ("PET") and polyarylether-ether ketone ("PEEK").

In another preferred embodiment, a seal including an elastomeric material and a fabric material is disclosed. The fabric material comprises a tubular braid of a plurality of strands. The strands include a polymeric material. The tubular braid has between about 48 and about 196 strands selected from a group consisting of a plurality of monofilament strands having a diameter of between about 0.001 and about 0.007 inch, and a plurality of multifilament strands having a denier of between about 75 and about 300. Preferably, the seal has a drag force of between about 0 and about 10 pounds and a leak rate of between about 0 and about 270 cc/min. The elastomeric material may have a durometer of between about 10 and about 80 shore A, an elastomeric material thickness of between about 0.003 and about 0.015 inches, and a cover factor of between about 0 and about 1. The seal has a density of strands to free space of between about 10% and about 70%, a constricted area having a length of between about 0.1 and about 2.0 inches, a braid angle of between about 0 and about 90 degrees, an initial seal diameter of between about 3 and about 10 mm, and a maximum seal diameter of between about 5 and about 18 mm. The elastomeric material may be selected from the group consisting of polyurethane, polyisoprene, silicone, Monprene™, Santoprene™ and other thermoplastic elastomers (TPE). The seal preferably has a diameter between about 4 mm and about 15 mm. The seal may have a minimum diameter and a maximum diameter, whereby maximum diameter is between about 3 times and about 5 times greater than the minimum diameter.

A method of gaining access to a surgical site within a body is also disclosed.

BRIEF DESCRIPTION OF THE DRAWING(S)

Preferred embodiments of the present disclosure will be better appreciated by reference to the drawings wherein:

FIG. 1 is a perspective view of an access apparatus in accordance with an embodiment of the present disclosure;

FIG. 2 is a second perspective view with cut-away portions showing the interior of the cannula of the access apparatus in accordance with the embodiment of FIG. 1;

DETAILED DESCRIPTION OF THE PREFERRED EMBODIMENT(S)

Figure 3:
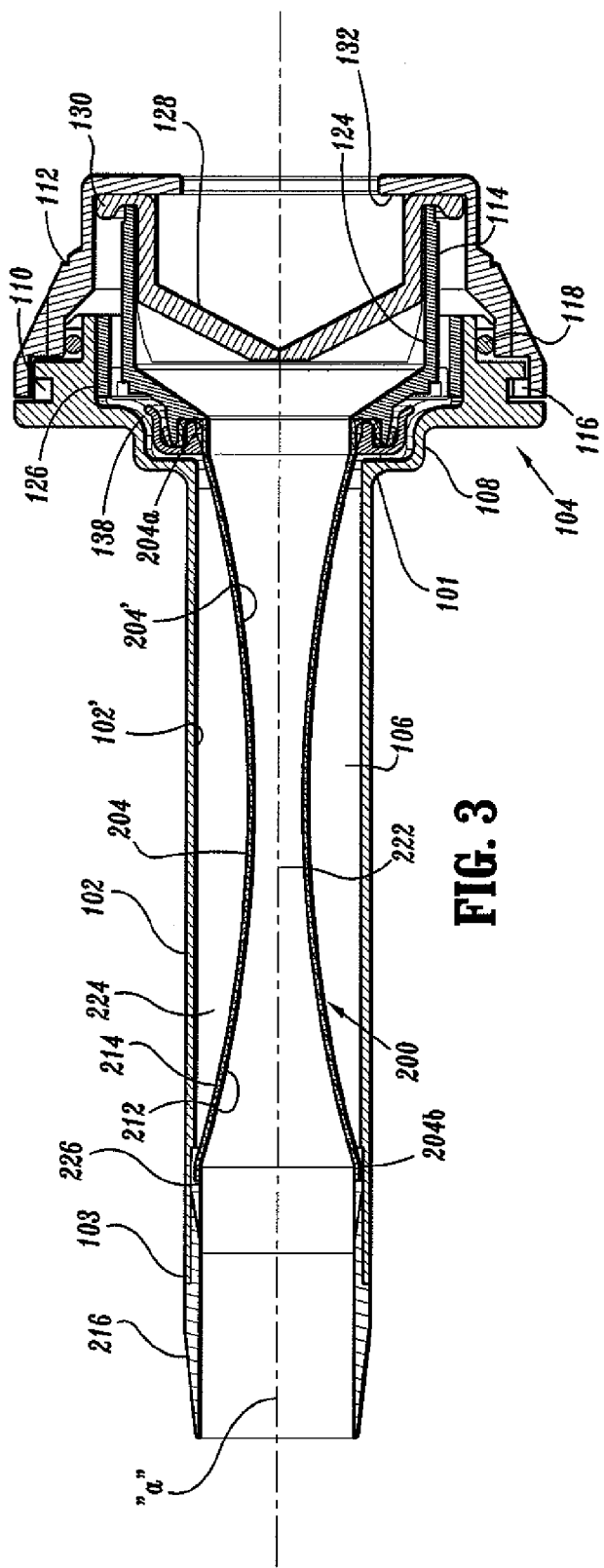
FIG. 3 is a side cross-sectional view of the access apparatus in accordance with the embodiment of FIGS. 1 and 2.

The access apparatus of the present disclosure provides a substantial seal between a body cavity of a patient and the outside atmosphere during insertion of an object through the apparatus. Moreover, the access apparatus of the present disclosure is capable of accommodating objects of varying diameters, e.g., instruments from about 4.5 mm to about 15 mm or more, and provide a gas tight seal with each instrument when inserted. This flexibility of the access apparatus greatly facilitates endoscopic surgery where a variety of instruments having differing diameters are often needed during a single surgical procedure.

The apparatus incorporates a seal assembly which permits the introduction and manipulation of various types of instrumentation adapted for insertion through a trocar and/or cannula assembly while maintaining a substantial fluid tight interface about the instrumentation to preserve the atmospheric integrity of a surgical procedure from gas and/or fluid leakage. Specifically, the seal assembly accommodates angular manipulation of the surgical instrument relative to the seal axis in addition to off-axis manipulation of the surgical instrument. This feature of the present disclosure desirably minimizes the entry and exit of gases and/or fluids to/from the body cavity. Examples of instrumentation include clip appliers, graspers, dissectors, retractors, staplers, laser probes, photographic devices, endoscopes and laparoscopes, tubes, and the like. Such instruments will be collectively referred to herein as "instruments or instrumentation".

The access apparatus may also be adapted to receive and form a seal about a physician's arm or hand during a hand-assisted laparoscopic procedure.

Referring now to the drawings, in which like reference numerals identify identical or substantially similar parts throughout the several views, FIGS. 1-6 illustrate an access apparatus in accordance with an embodiment of the present disclosure. For exemplative purposes, the access apparatus will be described in terms of a cannula assembly which is adapted for introduction, typically utilizing a trocar, within the abdominal cavity during a laparoscopic surgical procedure. However, it is appreciated that the access apparatus may be any apparatus suitable for introduction and passage of surgical objects into underlying tissue including, e.g., catheters, trocar assemblies, endoscopic portals, hand access devices, etc., through an incision or through a natural body opening.

Figure 4A:
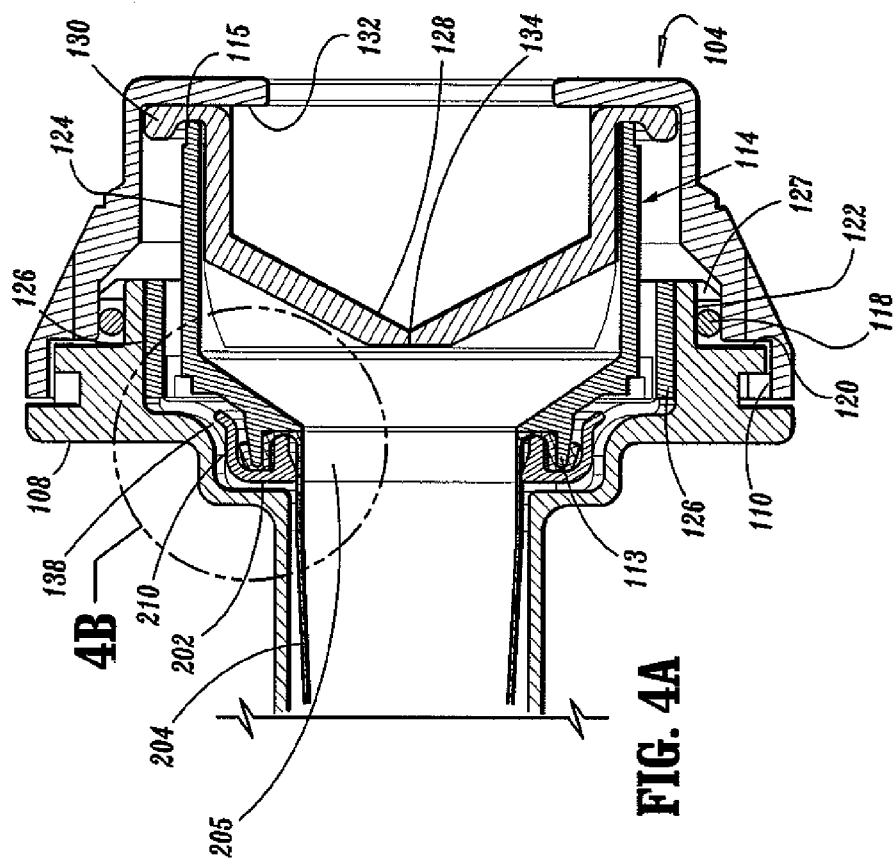
FIG. 4A is an enlarged cross-sectional view with portions removed of the access apparatus in accordance with the embodiments of FIGS. 1-3.
Figure 4B:
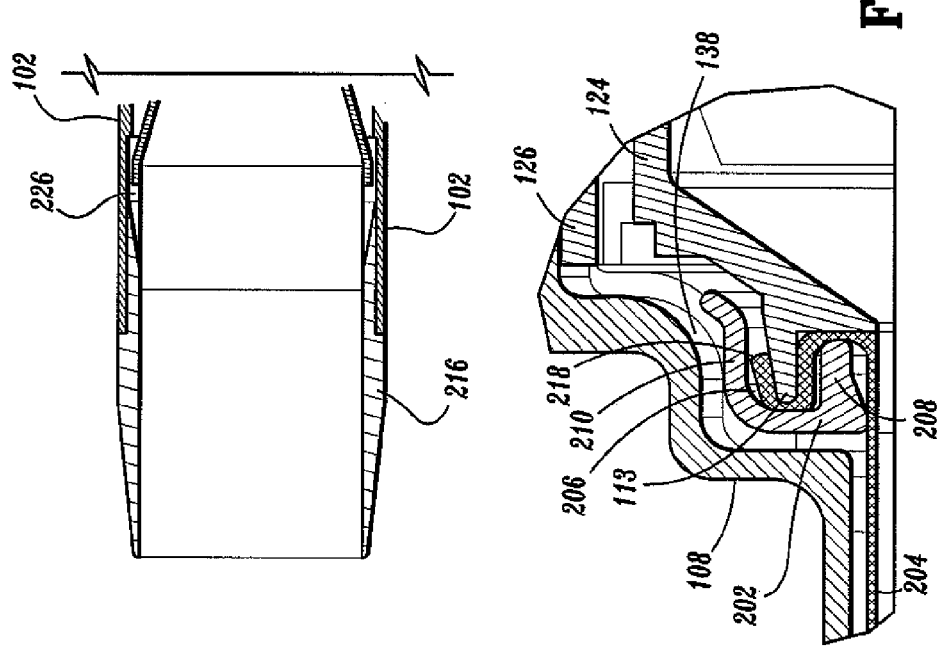
FIG. 4B is an enlarged cross-sectioned view illustrating the components of the connection of the seal within the cannula in accordance with the embodiment of FIGS. 1-4A.

With reference to FIGS. 3, 4A and 4B, in conjunction with FIGS. 1-2, cannula assembly 100 will now be described. Cannula assembly 100 includes a generally tubular member, similar to the conventional cannulas suitable for the intended purpose of accessing a body cavity and permit introduction of instruments therethrough. Cannula assembly 100 is particularly adapted for use in laparoscopic surgery where the peritoneal cavity is insufflated with a suitable gas, e.g., $CO_2$, to raise the cavity wall from the internal organs therein. Cannula assembly 100 is typically used with an obturator assembly, such as a sharp tipped trocar, which is an elongate instrument positionable within the cannula assembly 100. In FIG. 2, an obturator 1000 is shown partially introduced within cannula assembly 100. The obturator assembly 1000 may have a sharp end, a blunt end, or a tapered end for separating or dilating tissue, and is utilized to pass through, e.g., abdominal tissue, to facilitate introduction of the cannula assembly 100 within the abdominal cavity. Once access to the abdominal cavity is achieved, the obturator assembly 1000 is removed from the cannula assembly 100 to permit introduction of the surgical instrumentation utilized to perform the procedure.

In one preferred embodiment, access apparatus, i.e., cannula assembly IOU, includes cannula sleeve 102 having proximal and distal ends 101, 103 and cannula housing 104 mounted to the proximal end 101 of the sleeve 102. Cannula sleeve 102 defines a longitudinal axis "a" extending along the length of sleeve 102. Sleeve 102 includes an inner wall 102' that further defines an internal longitudinal passage 106 dimensioned to permit passage of a surgical object such as surgical instrumentation. Sleeve 102 incorporates sleeve flange 108 monolithically-formed (FIG. 3) at the proximal end 101. Sleeve 102 may be fabricated of stainless steel or another suitable rigid material such as a polymeric material or the like. Sleeve 102 may be clear or opaque. The diameter of sleeve 102 may vary, but, typically ranges from 5 to 15 mm. Sleeve flange 108 has a seal support 202 integrally formed with or attached to the sleeve flange 108. Sleeve Flange 108 further includes at least one circumferential recess or slot 110 within its outer surface. Circumferential slot 110 mates or cooperates with corresponding structure of cannula housing 104 to secure cannula sleeve 102 and cannula housing 104.

As best depicted in FIGS. 3, 4A and 4B, cannula housing 104 is connected to sleeve flange 108 of cannula sleeve 102. In one preferred embodiment, the connection is achieved through ultrasonic welding, adhesives, cements, etc. In the alternative, the cannula housing 104 and sleeve flange 108 may be connected through a bayonet, threaded or snap-fit coupling, e.g., incorporating a detent 116 of cannula housing 104 which is received within slot 110 of sleeve flange 108. An O-ring 118 is desirably disposed between an interior bearing surface 120 of cannula housing 104 and an exterior bearing surface 122 of sleeve flange 108 to minimize leakage of gases between the cannula housing 104 and sleeve flange 108 during use in the laparoscopic procedure.

A valve support 114 is mounted between cannula housing 104 and sleeve flange 108. Valve support 114 includes inner column 124 and outer collar 126 coaxially disposed about the inner column 124. Valve support 114 has a distal end 113 and a proximal end 115. Outer collar 126 is mounted against the internal surface of sleeve flange 10S and may be secured thereto with the use of adhesives, cements, etc. The O-ring 118 is captured between a depending leg 127 of outer collar 126, cannula housing 104 and sleeve flange 108, as best seen in FIG. 4A. A resilient valve 128 is supported within valve support 114. Resilient valve 128 includes a circumferential ledge 130 which is engaged by the proximal end 115 of inner column 124 and secured against an interior planar surface 132 of main housing 104 so that resilient valve 128 is supported within the interior of the inner column 124. Valve 128 may be of general cluck-bill configuration and defines an interior slit 134 which opens to permit passage of an object and closes in the absence of the object. The valve 128 is desirably a zero closure valve or a slit seal which is adapted to close in the absence of a surgical object to thereby prevent passage of insufflation gases through cannula assembly 100. In the alternative, valve 128 may be a flat disc-shaped valve, balloon valve, flapper valve, conical valve, etc. . . . In one preferred embodiment, valve 128 is the fabric seal disclosed in commonly assigned U.S. patent application Ser. No. 10/165,373, filed Jun. 6, 2002, now U.S. Pat. No. 6,702,787, "TROCAR SEAL SYSTEM", issued to Racenet et al. on Mar. 9, 2004, the entire contents of which are incorporated herein by reference. The seal disclosed in U.S. Pat. No. 6,702,787 may be a flat septum seal having a first layer of resilient material and a second fabric layer juxtaposed relative to the first layer. In yet a further alternative, valve 128 is preferably a fabric seal and is desirably arranged so as to have a constricted area. The fabric is desirably constructed of a material that forms a constriction or closure. The seal may also be molded with a resilient material so as to have a constriction. Other arrangements for valve 128 are also envisioned.

Cannula housing 104 desirably includes port 136, as best seen in FIG. 2, for connecting a stop cock to the cannula housing 104. The stop cock connects to an external source of insufflation gases for introducing insufflation gases into the body cavity of the patient through cannula sleeve 102. Port 136 is in communication with channel 138 defined adjacent the interior of sleeve flange 108 of cannula sleeve 102 (FIGS. 3, 4A and 4B). Channel 138 opens to longitudinal passage 106 of cannula sleeve 102.

Referring now to FIGS. 3-6, in conjunction with FIGS. 1-2, seal assembly 200 of cannula assembly 100 will be discussed in detail. Seal assembly 200 includes elongated seal 204 which extends from, the seal support 202. As best depicted in FIGS. 4A and 4B, seal support 202 is a generally annular element having an internal opening 205 and an outer trough 206 defined between inner and outer upwardly extending walls 208, 210 of the seal support 202 (FIG. 4B). The distal end 113 of valve support 114 is shaped to be received in outer trough 206. Proximal end 204a of elongated seal 204 is captured between outer trough 206 and the distal end 113 of the valve support 114 to mount the seal 204 as will be discussed. Alternatively or additionally, the seal 204 may be glued or adhered to the seal support 202 and/or sleeve flange 108. Seal support 202 is disposed within the internal boundary of sleeve flange 108 of cannula sleeve 102 when in the assembled condition of the apparatus. The seal support 202 may comprise a separate part attached to the cannula sleeve 102 or sleeve flange 108, or a part formed integrally with the sleeve flange 108 or cannula sleeve 102. In either case, the seal support 202 is desirably arranged so as to permit flow of insufflation gases through channel 138. As can be appreciated, the cannula sleeve 102 therefore includes the seal support 202 disposed within the cannula sleeve 102. The seal member 204 is secured at proximal end 204a within the cannula sleeve 102 via the seal support 202.

Figure 5:
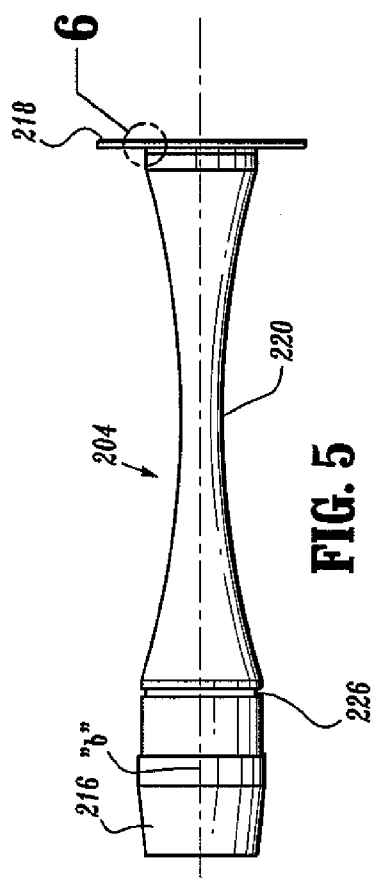
FIG. 5 is a side plan view of the seal assembly of the access apparatus in accordance with the embodiment of FIGS. 1-4B.
Figure 6:
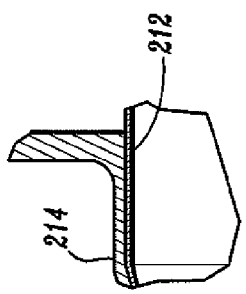
FIG. 6 is an enlarged isolated view in cross-section of FIG. 5, detailing the components of the seal of the access apparatus in accordance with the embodiment of FIGS. 1-5.

Elongated seal 204 comprises an elastomeric material, a fabric material, and/or combinations of these materials. The fabric material may comprise braided, woven, knitted, nonwoven materials. In a preferred embodiment, as best seen in FIGS. 5-6, elongated seal 204 incorporates a tubular braided fabric material 212. The tubular braided fabric may comprise strands of polyethylene, polypropylene, polyethylene, nylon, polyamides, polyglycolic acid, polyethylene teraphthalate (PET), glycolide-lactide copolymer, poly aryl ether-ether ketone, etc. and/or a combination of these strands. Metal strands, such as stainless steel, MP35N, nitinol and/or Titanium may also be used to form the fabric material. As used herein, the term "strands", "yarns" or ends include both monofilaments and multifilaments.

Variations of the tubular braid are envisioned. The tubular braid may include a variety of braid types with the number of strands (also called "ends of yarn" or "ends"), braid angle, strand diameter, and denier selected in accordance with desired characteristics of the fabric material. The tubular braided fabric material for the seal desirably has strands comprising a polymeric material, and having between about 48 and about 196 strands. The strands are desirably a plurality of monofilament strands having a diameter of between about 0.001 and about 0.007 inch, and a plurality of multifilament strands having a denier of between about 75 and about 300.

Preferred alternative examples of braided fabric materials are listed herein below:
1) 144 braided strands, with 72 of the strands comprising 0.003" PET (polyethylene terephthalate) monofilament and 72 of the strands comprising 100 denier PET multifilament.
2) 144 braided strands with 72 of the strands comprising 0.005" PET monofilament and 72 of the strands comprising 100 denier PET multifilament.
3) 144 braided strands of 0.003" PET or PEEK monofilament.

In the embodiment shown in FIGS. 1-6, the elongated seal 204 comprises a composite structure incorporating the tubular braid 212 and an elastomeric material 214. The elastomer is mounted to, formed on, or otherwise applied to the exterior surface of the braid, and preferably extends approximately the entire length of the tubular braid. The processes contemplated for applying the elastomer include spraying, dipping, injection molding, compression molding and extrusion processes including coextrusion, pulltrusion, corrugating as with vacuum or pressure etc. Preferably, the elastomer is formed so that the elastomer impregnates the fabric of the tubular braid, while leaving at least a portion of the fabric strands exposed at an interior surface of the braid 212. The elastomeric material 214 may comprise polyurethane, polyisoprene, or any suitable elastomer or resilient material. Other suitable elastomeric materials include polyurethane, silicone, polyisoprene, momprene, sanoprene, thermoplastic elastomers ("TPE"), material rubbers and any suitable materials.

In one preferred embodiment of the elongated seal 204, the fabric material comprises a tubular braid having 144 strands of 0.003" PEEK molded with polyisoprene. The polyisoprene alone has a coefficient of friction of about 0.9, whereas the composite structure had a coefficient friction of about 0.16.

With reference again to FIGS. 3-6, the configuration of one preferred embodiment of elongated seal 204 is depicted. Elongated seal 204 defines seal axis "b" which is coincident with axis "a" of cannula assembly 100. Elongated seal 204 incorporates tubular braid 212, which extends the length of the seal 204, and elastomeric material 214 mounted to, formed on, or otherwise applied to the tubular braid 212. Elongated seal 204 further includes cannula tip 216 secured to the distal end of the elongated seal 204. In a preferred embodiment, cannula tip 216 is directly secured to elongated seal 204 with an adhesive or formed during a molding process. Desirably, the elongated seal 204 is mounted in the cannula sleeve 102 with a degree of slack in the longitudinal direction. Upon insertion of an instrument though the elongated seal 204, and expansion of the tubular braid 212 in a radial direction, the tubular braid 212 contracts in a longitudinal direction. Mounting the elongated seal 204 with slack facilitates expansion of the elongated seal 204 without undue strain on the elongated seal 204.

Elongated seal 204 defines a slightly curved or circular arcuate profile sloping inwardly from its proximal end to a center 220 and then sloping outwardly from the center 220 to its distal end. This sloped, constricted configuration is created during manufacturing of the tubular braid and elastomer assembly. The tubular braid 212 and/or elastomeric material 214 may be formed in the curved shape and then joined to one another. Alternatively, the curved shape may be formed in the process of joining a constant diameter tubular braid and elastomer.

In the embodiment shown in FIGS. 1-6, the seal 204 has a circular concave shape, i.e., a curve having one radius. In other embodiments, curves having more than one radius may be used. The geometry and shape of elongated seal 204 affects sealing, snagging and push through force. Generally, shorter seal lengths decrease the chance of snagging and provide lower insertion forces. The shape of elongated seal 204 should balance sufficient sealing with push through forces. Elongated seal 204 is arranged so that an area of the seal around the center 220 is positioned to engage the instrument. The shape of elongated seal 204 and position of engagement with the instrument will define the approach angle of the tip of the instrument, relative to the seal 204. An approach angle approaching zero degrees, i.e., tangent to the surface of the seal, decreases snagging and push through force. A longer, gradually tapering, circular concave, or hyperbolic configuration is preferred, as such a shape creates a lower approach angle and lessens snagging and push through force. The fabric material, or elastomeric material, or both, are desirably pre-formed into the constricted or hourglass shape. Preferably, seal 204 includes an elongated shape that braid 212 assumes naturally, under tension, as this facilitates the manufacturing process.

The novel arrangement of the elongated seal 204 has many benefits. The elongated seal 204 seals around an instrument inserted into the passage 106. The seal 204 is disposed within the passage 106 of the cannula sleeve 102, and not within the cannula housing 104, so that the cannula housing 104 has a lower profile. The lower profile of cannula housing 104 effectively extends the useful length of the instrument which is inserted into the cannula assembly 100.

Furthermore, it is desirable to minimize the drag of the seal on the instrument so as to facilitate the manipulation of the instrument through the cannula assembly 100. The seal 204 desirably comprises a fabric material, arranged to ease insertion of the instrument. Preferably, the fabric material engages the instrument upon insertion. In embodiments incorporating elastomeric and fabric composite materials, the elastomeric material is preferably at least partially impregnated into the fabric material so that the seal 204 is largely elastomeric material at an outer surface thereof and possesses largely fabric strands at an inner surface thereof. The seal 204 may be entirely elastomeric material at an outer surface thereof and mostly fabric strands at an inner surface thereof. The fabric strands engage the instrument upon insertion, minimizing contact with the elastomeric material. Contact with the elastomeric material tends to increase the friction forces with the instrument. However, it is contemplated that elastomeric material may be formed on the inner surface of elongated seal 204. In certain embodiments, lubricants, coatings and/or other materials may be used to reduce friction.

The composite structure of certain preferred embodiments also reduces the tendency of the instrument to snag the fabric strands, even where the fabric strands are exposed at an inner surface of the seal 204. Without committing to any particular theory of operation, it is believed that the elastomeric material holds the strands in place, reducing the tendency of the instrument to catch the strands.

The elongate tubular shape of the seal 204 in certain preferred embodiments engages the instrument along the longitudinal axis "b" of the seal 204, increasing the contact area with the instrument, and improving sealing. The fabric material provides sufficient resiliency to seal with instruments in a range of sizes. The fabric material may be arranged to provide good sealing characteristics in the absence of any elastomeric material. The elastomeric material of certain preferred embodiments further provides sealing and resiliency for the seal 204.

Elongated seal 204 has an inner surface 204' that defines an internal passageway or seal passage 222, within the passage 106 of the cannula sleeve 102, which opens to the underlying body cavity to permit passage of an instrument. When the instrument is inserted, the fabric material and elastomeric material expands to enable the instrument to pass while establishing a sealed relation with the object. In the absence of an instrument, the seal 204 returns to its normal constricted configuration under the influence of the resiliency of elastomer 204 and fabric material.

Elongated seal 204 is coaxially arranged within cannula sleeve 102 to define an outer passageway 224 between the elongated seal 204 and the internal surface of cannula sleeve 102. The outer passageway 224 communicates with channel 138 and port 136. Elongated seal 204 further defines a gap 226 (FIG. 4A) or portion adjacent cannula tip 216 devoid of the elastomer. The gap 226 permits the passage of insufflation gases between outer passageway 224 and internal passageway 222 of elongated seal 204. Insufflation gases are introduced from port 136, through channel 138 through outer passageway 224, out gap 226 into the body cavity, to expand the body cavity. Alternatively or additionally, gap 226 permits the insufflation gases to pass from outer passageway 224 to internal passageway 222, as well as from internal passageway 222 into outer passageway 224, to substantially equalize the pressure within the two locations to allow the seal to adjust to instruments of different sizes. The gap 226 may be provided during the molding process or, alternatively, may be the result of a removal step where the elastomer is removed subsequent to molding to define the gap 226. The gap 226 may be created by perforating or forming a slit in the outer elastomeric material 214. It is further envisioned that cannula sleeve 102 may include an opening in its outer wall in communication with the outer passageway 224 to permit passage of gases to the abdominal cavity. This feature will be discussed in detail herein below.

The insufflation pressure may enhance the sealing ability of elongated seal 204, by allowing the insufflation gases to pass into outer passageway 224 between elongated seal 204 and cannula sleeve 102. If this feature is utilized, thin-walled fabrics and lower Durometer elastomeric materials, are preferred. As an alternative to gap 226, one or more slits may be formed in elongated seal 204 and arranged to open only when exposed to a predetermined pressure, to allow seal inflation. As another alternative, elongated seal 204 is devoid of an opening or openings whereby outer passageway 224 is inflated so as to constrict internal passageway 222 of elongated seal 204 and form a seal about an inserted instrument. In the alternative, insufflation gases may be introduced between seal 204 and the cannula sleeve 102 without inflating the seal by providing gas release structure e.g., through the gap 226, or in the form of an opening in the wall of cannula sleeve 102.

The access apparatus includes, in certain preferred embodiments, a fixation device at a distal end of the cannula sleeve. The fixation device desirably comprises the anchor disclosed in certain embodiments of U.S. Pat. No. 5,232,451, or the anchor disclosed in certain embodiments of U.S. Provisional Application No. 60/512,389, filed Oct. 17, 2003, the disclosures of which are both hereby incorporated by reference herein. In the alternative, a balloon anchor according to certain embodiments of U.S. Pat. No. 5,697,946 or 5,468,248 may be used, the disclosures of which are both hereby incorporated by reference herein.

The access apparatus according to the present disclosure may incorporate further features such as a skin seal or anchor, such as disclosed in certain embodiments of International Application No. WO 02/096307, the disclosure of which is hereby incorporated by reference herein. The access apparatus may be used with a radially expandable sleeve, as disclosed in certain embodiments of U.S. Pat. Nos. 5,431,676 and 5,183,464, the disclosures of which are both hereby incorporated by reference herein. In further embodiments, the cannula sleeve may include threads on an exterior surface thereof. As disclosed in certain embodiments of U.S. Pat. No. 6,224,608, the disclosure of which is hereby incorporated by reference herein, or a texture on an outer surface thereof. The cannula housing may define loops, flanges, or other structures for use as suture anchors. A person of ordinary skill will appreciate that all these features are well within the present disclosure.

In one preferred process of manufacture, tubular braided fabric material 212 includes a plurality of monofilament and multifilament polyethylene terephthalate (PET) fibers which are braided with, e.g., a braiding machine, to define a general tubular shape. Braiders for forming the tubular braided fabric material are commercially available. For example, Steeger machines from Steeger may be used (Körting Nachf. Wilhelm Steeger in Germany). Preferably, the tubular braid is formed in a tubular shape which defines a diameter approximating the maximum diameter of the elongated seal 204 during use. Thereafter, the tubular braided fabric material 212 is placed on a mandrel or pin, so that the mandrel or pin extends through the interior of the tubular braid 212. The mandrel has a shape which generally conforms to the internal passageway 222 of elongated seal 204 in its final state as depicted in FIG. 5, i.e., the shape of the mandrel generally corresponds to a desired end result of the tubular braid 212 depicted in FIG. 5.

Figure 9:
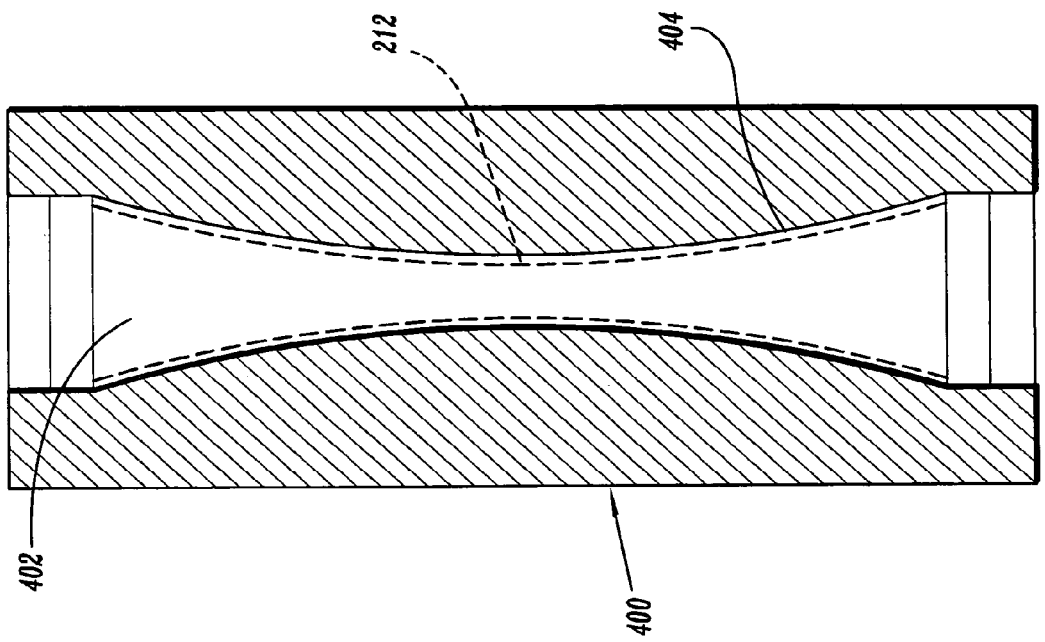
FIG. 9 is a schematic top plan view of a mold used in a preferred process for forming the seal in accordance with the embodiment of FIGS. 1-6.
Figure 8:
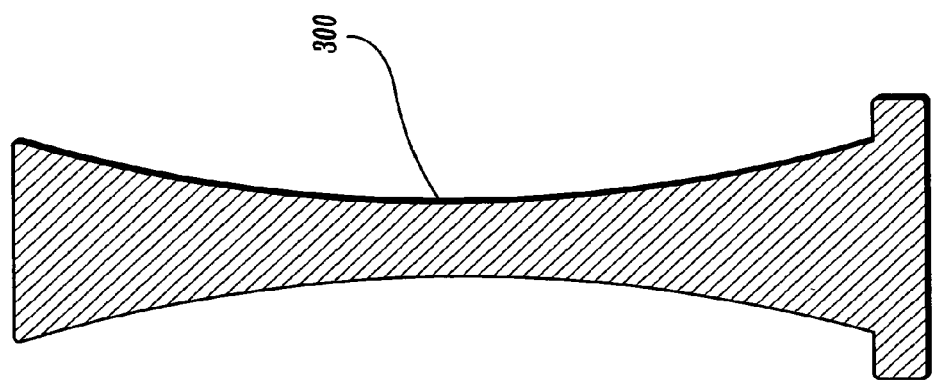
FIG. 8 is a schematic side plan view of a mandrel used in a preferred process for forming the seal in accordance with the embodiment of FIGS. 1-6.

FIG. 8 depicts a suitable mandrel 300 to form the desired hourglass shape. The tubular braid 212 is placed under tension to conform the braid to the shape of the mandrel. Thereafter, the shaped or sloped tubular braid 212 is subjected to a molding process to apply an elastomeric material 214 onto at least an exterior surface of the tubular braid 212. The preferred molding process is effectuated through, e.g., an injection molding process or a compression molding process. FIG. 9 illustrates a lower half of a mold 400 utilized to apply the elastomeric material. The mold 400 defines a mold cavity 402 corresponding to the general configuration of the tubular braid 212 (shown in phantom) to receive the braid 212 preferably with the mandrel 300. The mold 400 provides a slight clearance 404 about the periphery of the cavity 402 to receive the elastomeric material. The upper half of the mold 400 would be identical to the lower half depicted in FIG. 9.

With one preferred injection molding process, the shaped or sloped tubular braid 212 and mandrel are positioned within an injection mold having a shape generally corresponding to the shaped tubular braid 212 as discussed hereinabove. A molten elastomer is injected into the mold around the tubular braid 212. Upon curing, the elastomer coating 214 bonds to the exterior surface of the braid 212. As appreciated, the molten elastomer may migrate into the interstices of the braid 212 to fully impregnate the braid 212. However, the preferred process prevents complete communication of the molten elastomer to the interior surface of tubular braid 212. This is desirably accomplished by applying sufficient tension to the tubular braid 212 so as to increase contact with the mandrel, decreasing the braid 212 diameter, which increases the density of the braid, minimizing migration of elastomer to the inner surface of the tubular braid 212. At least a portion of the strands of the tubular braid are exposed at the inner surface of the tubular braid 212. A lubricious coating may be applied to the inner surface of the tubular braid 212, to further reduce insertion forces. Lubricious coatings including hydrogels and medical fluid may be used. Preferred materials for injection molding include thermoplastic elastomers ("TPE"). Any suitable elastomer may be used.

Alternatively, a compression molding process may be utilized to form the elastomeric material 214. In accordance with one preferred process, the tubular braid 212 and mandrel 300 are placed within a compression mold (such as mold 400 of FIG. 9) having a mold cavity conforming to the desired shape for the tubular braid 212. Heat and pressure are applied so that the molten elastomer is then compressed within the tubular braid 212 to cover at least the exterior surface of the tubular braid 212 and impregnate interstices of the braided fabric material. Pressure may be applied using mechanical pressure and/or a vacuum. Preferably, complete communication of the molten elastomer to the interior surface of tubular braid 212 is avoided, as well—the benefits of which are discussed hereinabove. Any suitable elastomer may be used. One preferred elastomer for compression molding is polyisoprene.

It is envisioned that during either the injection or compression molding processes, cannula tip 216 may be positioned within the molds and secured to the tubular braid 212 through an overmolding step. It is also envisioned that the cannula tip 216 be formed using injection molding as the elastomer is injected, or serially before or after the elastomer is injected, over the braid 212. In addition, the cavity 402 of the mold 400 may include spaces for the elastomeric material to build up, forming elastomeric features on the seal assembly 200. The tubular braid 212 desirably extends beyond the end of the mold, for clamping and/or tensioning the tubular braid 212.

Referring again to FIGS. 3-6, the proximal end of elongated seal 204 has a circumferential flange 218. Flange 218 is monolithically formed from the elastomeric material 214 during, e.g., the injection or compression molding processes. Circumferential flange 218 is received within trough 206 of seal support 202 and may be secured within the trough 206 with the use of adhesive, cements or the like. As discussed hereinabove, the distal end 113 of inner column 124 of valve support 114 secures circumferential flange 218 within seal support 202 by engaging the flange 218 to secure it within the trough 206 along with the proximal end of the fabric material 212.

In yet another preferred method, the tubular braid 212 may be dipped into a pool of elastomeric material. A preferred elastomer is urethane. The urethane wicks to the interior surface of the tubular braid 212 to form a urethane layer at the inner surface of the tubular braid 212. The tubular braid 212 is then inverted such that the elastomeric material is largely disposed on the exterior of the tubular braid 212. The tubular braid 212 is placed under tension to form a constricted shape along its length to shape the braid, and heat is applied to the assembly. The assembly is cured under the tensioned stated to define desired curved configuration of the elongated seal 204.

Alternatively, in accordance with another process, an elastomer jacket may be separately formed in the desired sloped or tapered configuration and then adhered or otherwise bonded to the outer surface of the tubular braid 212 to impart the desired tapered configuration to tubular braid 212.

In another embodiment, the tubular braid 212 may include either monofilament fibers or a combination of monofilament and multifilament fibers, which are wrapped with strands such as elastomeric strands.

Irregardless of the above described processes employed, elastomeric material 214 serves as a further barrier to the insufflation gases. Elastomeric material 214 also provides further resiliency of the elongated seal 204. The braid expands in receiving instruments, forming a fluid tight seal about the instrument, and the braid returns to its initial constricted arrangement subsequent to removal of the instrument. The elastomeric material 214 also expands in receiving the instrument and returns to an initial constricted arrangement upon removal of the instrument.

It is further contemplated that an elastomeric material may be applied to cover the inner surface of tubular braid 212 in addition to the elastomeric material 214 at outer surface of the braid 212. Preferably, the inner layer has a relatively high durometer to minimize resistance to the inserted instrument, whereas the outer layer preferably has a relatively lower durometer. The inner layer may incorporate protrusions to fill any gaps between elongated seal 204 and the inserted instruments. The inner and outer elastomeric materials may be formed using injection molding, extrusion or co-extrusion processes, injection coining and compression molding.

As discussed hereinabove, tubular fabric 212 may also be formed by a weaving process. The fabric is initially woven into a tube-like structure with the "ends" running in the longitudinal axis of the seal, and the "fill" running in the opposite direction. The fill strands, at least in the center of the seal, comprise LYCRA (trademark of I.U. DuPont and Nemours Company) strands. The LYCRA strands form the constricted shape for the seal. The LYCRA serves to facilitate the establishment of a seal about the instrument and controls puckering of the fabric, which may lead to leakage. Various materials are contemplated for the weave including 80 denier PET, 20 denier PET, etc. with all or less than the entire fill comprising LYCRA. It is further contemplated that several strands of PTFE or polypropylene may be intermingled amongst the various other longitudinally-running ends to reduce friction and facilitate passage of the instrument through the woven seal. PTFE and polypropylene by their respective natures have a low-friction characteristic. Desirably, the seal includes a woven fabric material and an elastomeric material. The woven fabric may further include pleats defined in the interior of the tubular fabric. The pleats may tend to eliminate gaps and other avenues between elongated seal 204 and the surgical instrument.

Other arrangements and methods of manufacture for elongated seal 204 are also envisioned. Some exemplative arrangements and processes of manufacture directed to the fabric material are discussed below:

Braid Examples

1. Spool wind 72 spools of 0.003" polyester (PET) monofilament clear with no lubricant on a winding apparatus such as a Fletcher spool winder. The winding apparatus should be tensioned appropriately. Spool up 72 ends of a 100 denier PET with no lubricant/sizing, with 100 Denier, 36 end with high interlacing, PET, for a total of 144 ends. Next load up both sets of 72 spools on a 144 carrier machine with low tension spring systems. The spools are loaded in a pattern to create a fabric having alternating ends of monofilament and multifilament. The braid is manufactured without a mandrel at a pick count of 28 picks per inch. "Picks per inch" is defined herein as the number of intersections between ends, per inch of fabric. This creates a tube of 144 ends at approximately 3-4 mm in diameter with a cover factor of 70%. This tube is then impregnated with a polymer in order to create a composite seal structure using any of the methods discussed above. The composite tube has the ability to stretch radially 400-500%. The length of the braided tube shortens by 15-20 when stretched to 500% the original diameter.

2. Spool wind 72 spools of 0.003" Teflon (PTFE) monofilament clear with no lubricant. Spool up 72 ends of a 100 denier PET with no lubricant/sizing and 100 Denier, 36 ends with high interlacing, PET for a total of 144 ends. Next load up both sets of 72 spools on a 144 carrier machine with low tension spring systems. The spools are loaded in a pattern to create a fabric having alternating ends of monofilament and multifilament. The braid is manufactured without a mandrel at a pick count of 28 picks per inch. This creates a tube of 144 ends at approximately 3-4 mm in diameter with a cover factor of 70%. This tube is then impregnated with a polymer in order to create a composite seal structure (using any of the methods discussed above). The composite tube has the ability to stretch radially 400-500%. The length of the braided tube shortens by 15-20 when stretched to 500% the original diameter. The PTFE monofilaments create a low drag inner surface to the seal to reduce push through force.

3. Spool wind 144 spools of 0.003" polyester (PET) monofilament clear with no lubricant. Next load up both sets of 144 spools on a 144 carrier machine with low tension spring systems. The braid is manufactured without a mandrel at a pick count of 29 picks per inch. This creates a tube of 144 ends at approximately 3-4 mm in diameter with a cover factor of 60%. This tube is then impregnated with a polymer in order to create a composite seal structure (using any of the methods discussed above). The composite tube has the ability to stretch radially 400-500%. The length of the braided tube shortens by 15-20 when stretched to 500% the original diameter. The 100% monofilament braid has higher abrasion resistance and is less prone to snagging due to the increased stiffness the monofilaments add to the fabric.

Weave Examples

1. A narrow fabric loom is set up with 200 denier PTFE filaments in the warp direction at a warp density of 50 ends per inch. The loom is configured to weave a continuous tube. Spandex fill yarns of 40 denier are woven into the fabric at a constant fill density of 150 picks per inch. By manipulating the fill yarn tension, the fabric tube "power" or squeeze force may be selectively adjusted.
2. A narrow fabric loom is set up with 200 denier PTFE filaments in the warp direction at a warp density of 50 ends per inch. The loom is configured to weave a continuous tube. Spandex fill yarns of 80 denier are woven into the fabric at a constant fill density of 60 picks per inch. The fill yarn tension may be manipulated to change the fabric tube "power" or squeeze force.
3. A narrow fabric loom is set up with 200 denier PTFE filaments in the warp direction at a warp density of 50 ends per inch. The loom is configured to weave a continuous tube. Spandex fill yarns of 40 denier are woven into the fabric at a variable fill density of 50 to 150 picks per inch. The fill yarn density may be manipulated to change the fabric tube "power" or squeeze force over given controlled fabric lengths.
4. A narrow fabric loom is set up with 200 denier PTFE filaments in the warp direction at a warp density of 50 ends per inch. The loom is configured to weave a continuous tube. Spandex fill yarns of 40 denier are woven into the fabric at a constant fill density of 150 picks per inch. The diameter of the tube may be adjusted by changing the warp density. The larger less dense fabric can become smaller in diameter which in turn reduces the fill yarn tension and reduces power.

Knit Examples

1. A one inch head circular knitting machine from Lamb Knitting Corporation with 36 needles per inch was set up to knit a tube using a 200 Denier polyester yarn. The higher the needle density, the more dense the fabric. Denser fabric tends to resist poke through and snagging. Knit fabrics are physically more flexible than braids or weaves. The knit structure is a stretchy reinforcing material able to conform to the seals shape and stretch open when required to pass tools through the tube.
2. A one inch head Lamb circular knitting machine with 36 needles per inch was set up to knit a tube using a 200 Denier Teflon yarn. The higher the needle density, the more dense the fabric. Denser fabric tends to resist poke through and snagging. Teflon reduced tool push through drag.
3. A double needle bar warp knitting machine was set up to knit a tube. The warp knitter has 28 needles per bar and PET 200D yarn. Higher needle densities create a denser tube fabric. The warp knit structure is a stretchy reinforcing material able to conform to the seals shape and stretch open when required to pass tools through the tube. Warp knits are highly durable. A seam is created when warp knitting a tube.

In use of the apparatus, in laparoscopic surgery, for example, the underlying body cavity, e.g., the abdominal cavity is insufflated, as is known, to expand the body cavity and displace the abdominal wall from the underlying organs therein. Cannula assembly 100, with obturator 1000 positioned therein, is advanced within the abdominal tissue to penetrate the abdominal wall. Obturator 1000 is removed while cannula assembly 100 remains within the incision. Surgical instruments are advanced within cannula assembly 100, opening valve 128, and entering internal passageway 222 of elongated seal 204. The instruments are advanced whereby the elongated seal 204 engages the instrument and expands outwardly to form a fluid tight seal about the exterior surface of the instrument. The instrument is utilized to perform the desired procedure. The configuration of elongated seal 204 permits the seal to move relative to axis "a", as the instrument is manipulated during the surgery. As discussed below in connection with FIGS. 10 and 11, the area of seal 204 that engages the instrument is greater for an instrument with a larger diameter, e.g. instrument 10' in FIG. 11, as compared to an instrument with a smaller diameter, e.g., instrument 10 in FIG. 10. During the procedure, insufflation gases are introduced through outer passageway 224. The gases pass through gap 226 of elongated seal 204 to enter the body cavity to maintain insufflation of the body cavity. The insufflation gases also pass through gap 226 from outer passageway 224 to internal passageway 222 and from internal passageway 222 to outer passageway 224 of elongated seal 204 to substantially equalize pressure between the outer passageway 224 and internal passageway 222 of elongated seal 204 as instruments are inserted and removed.

The present disclosure contemplates changes to the structure of the seal. For example, the fabric material of the elongated seal may comprise any suitable fabric structure. The fabric material of elongated seal 204 must have adequate snag resistance, adequate sealing, and generate acceptable push-through forces upon insertion and removal of an instrument. Fabric materials have certain characteristics that affect the snag resistance, sealing and push through forces, including the material modulus, size and type of strands (also known as yarns), density, power, and geometry of the fabric structure.

As discussed in greater detail hereinbelow, elongated seal 204 is arranged in a constricted shape, e.g., a circular concave, a hyperbolic, or an hourglass shape, so that a portion of the seal engages an instrument upon insertion of the instrument into the seal. The fabric structure is desirably selected so that the strands largely extend in the longitudinal axis of the elongated seal 204, to reduce snagging. The fabric structure should be selected with a tortuous fluid path, as these fabric materials have lower permeability and greater sealing around the instrument.

The fabric is desirably formed from a plurality of polymeric strands which conform to the instrument inserted without pocketing. The strands for the fabric can be metal, such as stainless steel, MP25N, nitinol and/or Titanium. Pocketing is the formation of an indentation in the fabric when engaged by an instrument and tends to result in greater snagging of the fabric by the instrument. Materials with a lower modulus of elasticity are desirable for their greater sealing characteristics, whereas higher modulus materials are desirable for their lower push through forces and lower snagging. The strands of the fabric desirably has a modulus greater than or equal to 700,000 PSI, for acceptable pocketing and snagging. The smaller the size of the strands that form the fabric, the greater sealing and lower push through forces achieved. However, multifilament strands over 100 Denier and monofilament strands greater than 0.003 inches in diameter are desired, for acceptable snag resistance.

Fabrics which are denser and have higher cover are desired. Tighter or more dense fabrics have lower permeability (defined by cc/cm^2/min). Denser fabrics create a more durable, better sealing structure, with less snagging. Denser, tighter fabrics, having smaller pores, resist snagging, whereas more open fabrics allow instruments to "poke through" the pores and snag. Denser fabrics are formed from a greater number of strands. Fabric materials with greater density produce lower push through forces, as the instrument tends to slide on the strand surfaces. This is surprising, as normally greater friction results from greater surface contact.

Preferably, the density of the fabric, when an instrument is inserted and the seal is expanded to its greatest size is more than 48 strands per inch (also known as "ends per inch"), but not more than 200 strands. The number of ends per inch is measured around the fabric perimeter. If the number of ends per square inch is too high, the constricted shape or hourglass shape can not be formed without puckering, which tends to cause leaking. To increase the density of the fabric, while improving the ability of the fabric to form a constricted shape or hourglass shape, a greater number of smaller yarns may be used. However, multifilament strands over 100 Denier and monofilament strands greater than 0.003 inches in diameter are desired, for acceptable snag resistance.

The fabric desirably has enough "power" to create an effective seal without increasing the push through forces and snagging to an unacceptable level. "Power" defines the level of "squeezing force" the seal applies to an instrument inserted into the seal. If the power level of the fabric is high, the seal squeezes the instrument with more force. Higher power improves sealing around the instrument.

The fabric material may comprise strands of multifilament, monofilament, or a combination of multifilament and monofilament strands. The permeability of the fabric material, as defined by cc/cm^2/min, is lower for multifilament fabrics than monofilaments. Multifilament strands create a high resistance to fluids and greater sealing, whereas monofilaments create a low resistance to fluids and leak more. Monofilaments have a greater resistance to snagging as compared to multifilaments.

Runners can be used on the fabric structure (e.g., knits, weaves, braids), extending in the axial direction of the seal, down the length of the seal. Runners greatly improve snag resistance. The runners desirably comprise higher modulus monofilaments of, for example, polypropylene, PEEK, polyester, nylon or other suitable materials. The runners also add radial stiffness to the fabric structures. This stiffness reduces pocketing and snagging. Runners increase the strand surfaces which are engaged by the instrument and in turn reduce push through forces.

The elongated seal is preferably formed from a composite structure of fabric material and a resilient material, preferably comprising an elastomeric material. The elastomeric material may comprise any suitable material. The elastomeric material is used to cover and shape a "zone" of the seal. The elastomeric material 214 and fabric of the tubular braid 212 form a composite structure. The sum of the components, i.e., fabric material and the elastomeric material, define the final seal geometry, create the power for sealing, and have significant effects on the push through force and snag resistance. The elastomeric material facilitates holding the tubular fabric structure together, diminishing the chance of snagging.

Elastomeric materials with higher Durometer (a measure of hardness), above 70 shore-A, tend to produce better seals. Creep is lowered and tacky surface properties diminish as Durometer increases. Higher Durometer elastomeric materials produce seals with higher power, and better sealing. Thicker films of elastomeric material also produce more power for the seal. However, these characteristics must be balanced against greater push through forces.

It is desired that the surfaces of the strands of tubular braid 212 are available or presented at the inner surface of elongated seal 204, to contact the instrument to reduce the push through forces. The harder, higher modulus polymers used to make the strands tend to be quite lubricious, reducing friction, as compared to elastomeric material.

The elastomeric material must substantially fill the "gaps" in the fabric material in order to create a film or membrane throughout the entire fabric surface. A complete film will assure that fluid does not pass through the seal. A seal with a thinner wall is desirable because such a seal leaves less space for fluid to escape.

The composite seal structure should be flexible and conformable enough to move with the instrument, which improves sealing and reduces the chance of pocketing and snagging. These characteristics are governed by fabric construction, strand type, elastomeric material type, and seal geometry. Thus, the fabric construction, strand type, elastomeric material type, and seal geometry should be selected to form a seal with the desired sealing and snagging. Thinner more compliant fabric and elastomeric material composite structures also decrease push through forces.

Figure 7:
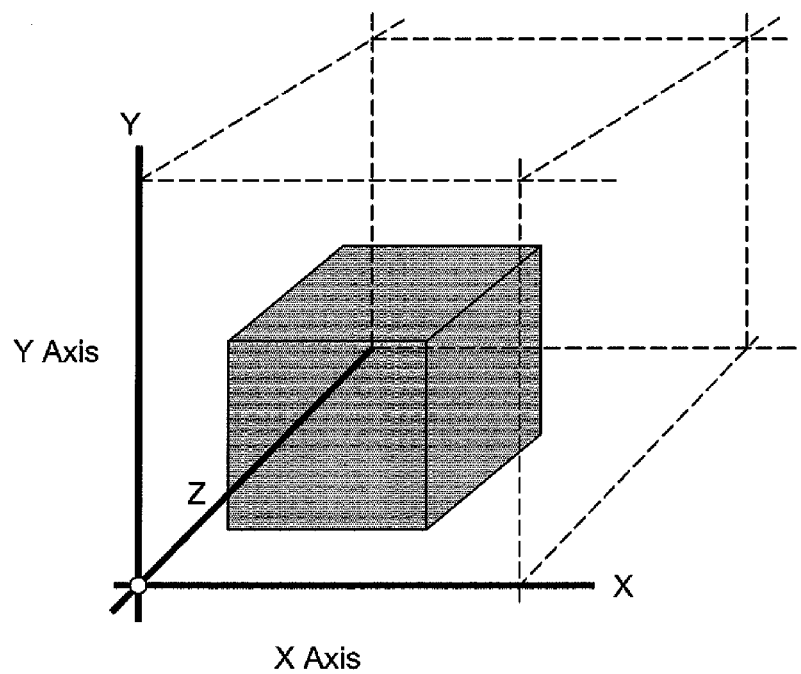
FIG. 7 is a chart illustrating a preferred range of various design parameters for forming the seal of the access apparatus in accordance with the embodiment of FIGS. 1-6.

FIG. 7 is a design chart illustrating a three dimensional envelope for a preferred seal composite structure. In all cases, the X, Y, and Z axis variables are adjusted, compensated and interchanged to create a design volume (dv) for optimum seal design. Anything outside of the dv may still produce a working seal, however, with less attractive working features such as higher push through forces, less snag resistance, more leakage, or the other characteristics discussed above. The optimum features for the seal (quantified values such as loads, Durometer, volume fractions) are defined by the desired working requirements including drag or push through force (0-10 lbs) and leak rate (0-270 cc/min) to be achieved. The working requirements of elongated seal 104 are encompassed by the Z-axis variables. The X-axis variables are (1) the seal diameter from the initial to the expanded diameter and (2) the number of yarns in the seal. The Y-axis variables are (1) durometer, (2) surface cover factor, (3) density of yarn to free space, (4) thickness of polymer, (5) geometry of the seal zone and (6) braid angle. The X-axis variable and the Y-axis variables are optimized to produce the desired Z-axis parameters for elongated seal 204.

In the design volume shown above, the preferred seal structure will have a drag force of 0-5 pounds, a leak rate of 0-270 cc per minute, an elastomeric material durometer of 10-80 shore A, frictional properties as per ASTM D1894 (plastic film and sheeting) between 0.07 and 0.5, a cover factor of 0-1, a density of strands to free space of 10-70%, a elastomeric material thickness of 0.003-0.015 inches, a constricted area length of 2-0.1 inches, a braid angle of 0-90 degrees, an initial to expanded seal diameter of 3-18 mm, and a strand count of 30-200.

A more preferred seal structure will have a drag force of 0.5-1.5 pounds (when used with larger sized instruments having a diameter of about 10-14 mm), a leak rate of 0-120 cc per minute, an elastomeric material durometer of 10-30 shore A, a coefficient of friction of 0.07-0.18, a cover factor of about 1, a density of 70%-100%, an elastomeric material thickness of 0.003-0.010, a constricted area length of 0.5-1.5 inches, a braid angle of 0-60 degrees, an initial to expanded seal diameter of 4-15 mm and a strand count of 100-160.

Figure 10:
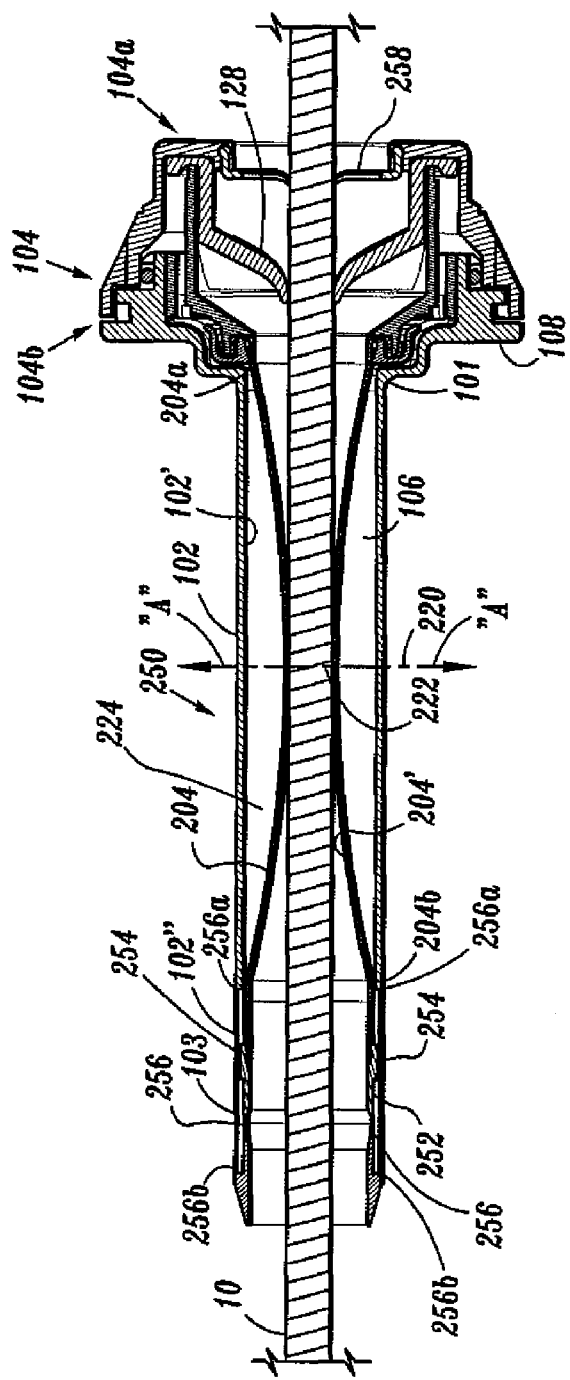
FIGS. 10-11 are cross-sectional views of an access apparatus in accordance with a further embodiment of the disclosure.
Figure 11:
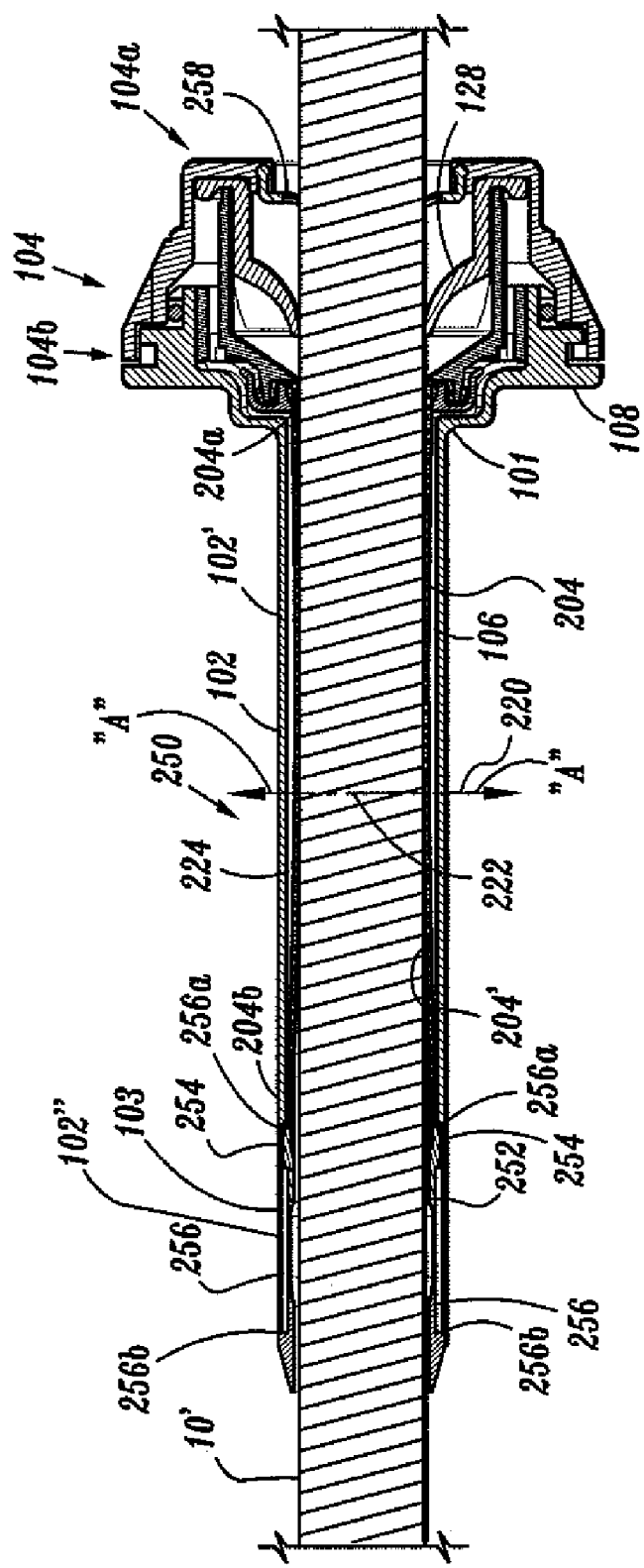

FIGS. 10-11 illustrate an alternate embodiment of the present disclosure. This access apparatus 250 is substantially similar to the embodiment of FIGS. 1-6, but incorporates a seal mount 252 disposed within cannula sleeve 102 adjacent distal end of cannula sleeve. Seal mount 252 is affixed to the distal end of elongated seal 204, in the same manner as discussed above in connection with cannula tip 216, and is mounted for axial movement within the cannula sleeve 102 between a retracted position shown in FIG. 10 and an extended position shown in FIG. 11. In addition to defining proximal seal end 204a, elongated seal member 204 also defines distal seal end 204b. As described above with respect to FIGS. 3-6, the seal member 204 is secured at proximal end 204a within the cannula sleeve 102 via the seal support 202, which includes the proximal seal end 204a being secured within the cannula sleeve 102. As illustrated in FIGS. 10 and 11, the distal seal end 204b of elongated seal member 204 is secured to the seal mount 252. Specifically, seal mount 252 includes opposed keys 254 which are received within internal recesses 256 of cannula sleeve 102. Desirably, recesses 256 do not extend through to the exterior surface 102" of the cannula sleeve 102. Keys 254 traverse recesses 256 to permit seal mount 252 and the distal end 204b of elongated seal 204 to move in an axial direction, as illustrated by arrows "A". In this manner, elongated seal 204 may be sufficiently taut when mounted within cannula sleeve 102, i.e., substantially devoid of excess slack material. FIG. 10 illustrates the arrangement of elongated seal 204 and seal mount 252 when a relatively small diameter instrument 10 is positioned within access apparatus 250. As described above with respect to FIGS. 3-6, elongated seal 204 includes inner wall 204' defining longitudinal opening or internal passageway 222 for passage of a surgical object. As shown, an area of elongated seal 204 around the center 220 forms a fluid-tight-relationship with the instrument 10 while seal mount 252 is in a first position. With reference to FIG. 11, upon insertion of a larger diameter instrument 10', seal mount 252 moves in a proximal retracting motion to permit an area of elongated seal 204 around the center 220 to expand while still maintaining a fluid tight seal about the instrument 10'. The area of seal 204 that engages the instrument 10' is greater in FIG. 11, as compared to FIG. 10. Access apparatus 250 may also include a septum seal 258 mounted at the proximal end 104a of cannula housing 104 to provide additional sealing capabilities. Septum seal 258 may be any of the seal arrangements described hereinabove. Both the septum seal 258 and duckbill valve 128 shown open to accommodate the instrument inserted into the access apparatus.

Thus, seal member 204 is at least partially disposed within the inner wall 102' of the cannula sleeve 102. The seal member 204 is elongated extending along the longitudinal axis "a" of the cannula sleeve 102. The seal member 204 has inner surface 204' that defines seal passage 222 and is adapted to form a substantial sealing relation with a surgical object, e.g., surgical instruments 10 or 10'. The seal mount 252 is secured to the seal member 204 and is disposed adjacent the distal end 103 of the cannula sleeve 102. The seal mount 252 is mounted for longitudinal movement relative to the cannula sleeve 102 to accommodate passage of the surgical object 10 or 10' through the seal passage 222 of the seal member 204. The seal mount 252 has a configuration that includes key or keys 254 depending from the seal mount and the inner wall 102' of the cannula sleeve 102 includes recess or recesses 256. The recess 256 defines a proximal key stop member 256a and a distal key stop member 256b in the inner wall 102' of the cannula sleeve 102. The key 254 is accommodated within the recess 256 and is dimensioned to traverse the recess 256 during longitudinal movement of the seal mount 252 with respect to the cannula sleeve 102 such that the seal mount 252 retains the configuration during traversal of the key or keys 254 in the recess or recesses 256 between the proximal and distal stop members 256a and 256b, respectively, during longitudinal movement of the seal mount 252 with respect to the cannula sleeve 102.

The seal mount 252 is dimensioned and adapted to move in a general proximal longitudinal direction (.e.g, along axis "a" of FIG. 3) upon insertion of the surgical object 10 or 10' through the passage 222 of the seal member 204 to facilitate displacement of the inner surface 204' and alter a size of the seal passage 222, e.g., axially in the direction of arrows "A" in FIGS. 10 and 11. As illustrated in FIGS. 10 and 11, the seal mount 252 is at least partially disposed within the cannula sleeve 102. The access apparatus 250 includes cannula housing 104 at proximal end 104a thereof and the cannula sleeve 102 extends distally from distal end 104b of the cannula housing 104. The cannula housing 104 includes zero closure valve 128 adapted to substantially close in the absence of the surgical object 10 or 10'.

Figure 12:
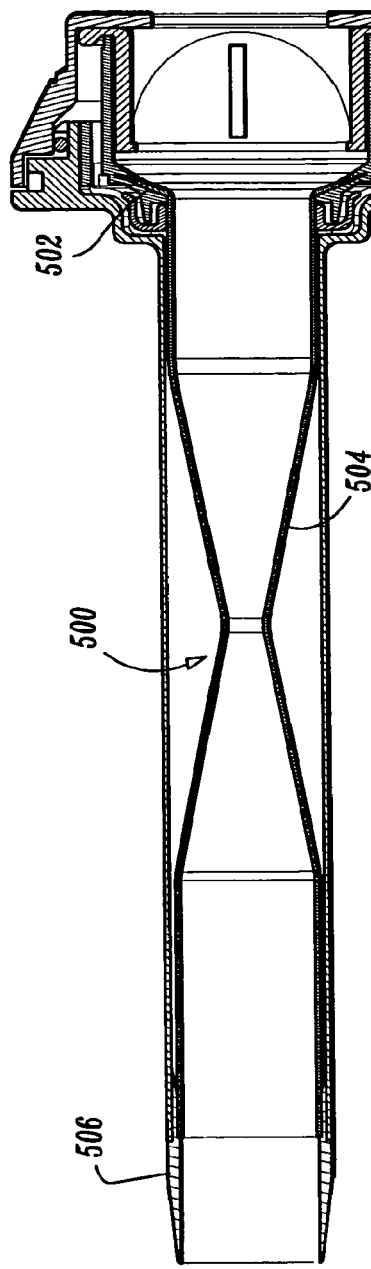
FIG. 12 is a side cross-sectional view of an access apparatus in accordance with another embodiment of the disclosure.
Figure 13:
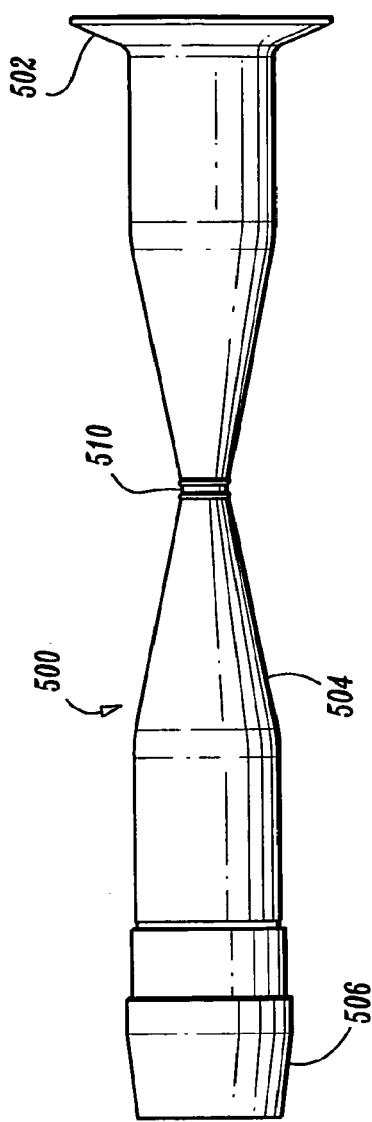
FIG. 13 is a side plan view of a seal assembly of an access apparatus in accordance with the embodiment of FIG. 12.
Figure 14:
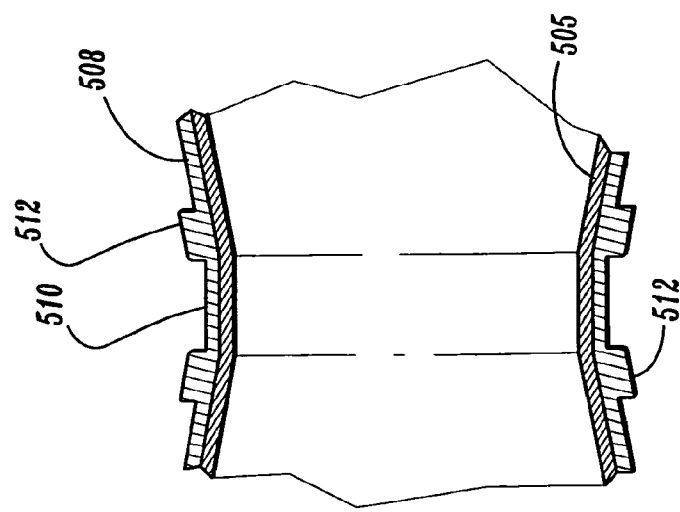
FIG. 14 is an enlarged isolated view in cross-section of the constricted area of the seal assembly in accordance with the embodiment of FIGS. 12 and 13.

FIGS. 12-14 show a cannula assembly according to an alternate embodiment of the present disclosure. Elongated seal 500 includes proximal flange 502, tubular member 504 extending from the proximal flange 502 and cannula tip 506 mounted to the distal end of the tubular member 504. Tubular member 504 includes a braided fabric 505 with an external elastomer coating 508. Proximal flange 502 may be integrally formed with elastomer coating 508 or affixed to the proximal end of tubular member 504. Elongated seal 500 includes a general hourglass shape tapering inwardly from the proximal end to a construction 510 and tapering outwardly from the construction 510 to the distal end of the tubular member 504. The hourglass configuration is formed during the manufacturing process by placing the tubular braid on a corresponding hour-glass shaped mandrel and forming the elastomeric material over the braid in accordance with any of the techniques discussed hereinabove.

In a preferred embodiment, elastomer coating 508 incorporates a pair of rib portions 512 adjacent construction 510. Rib portions 512 provide an area of increased elastomer thickness to effectively increase the resiliency of central portion 510 of tubular member 504. This increased resiliency ensures the formation of a fluid-tight seal about the instrument and facilitates return of the central section 510 to its original diameter subsequent to removal of an instrument. Rib portions 512 may be incorporated within the mold (compression or injection) as correspondingly dimensioned recesses in the mold which receive the elastomer over-flow. Alternatively, rib portions 512 may be separate elastomer bands adhered to the outer surface of central section 510 of elongated seal 500.

Figure 15:
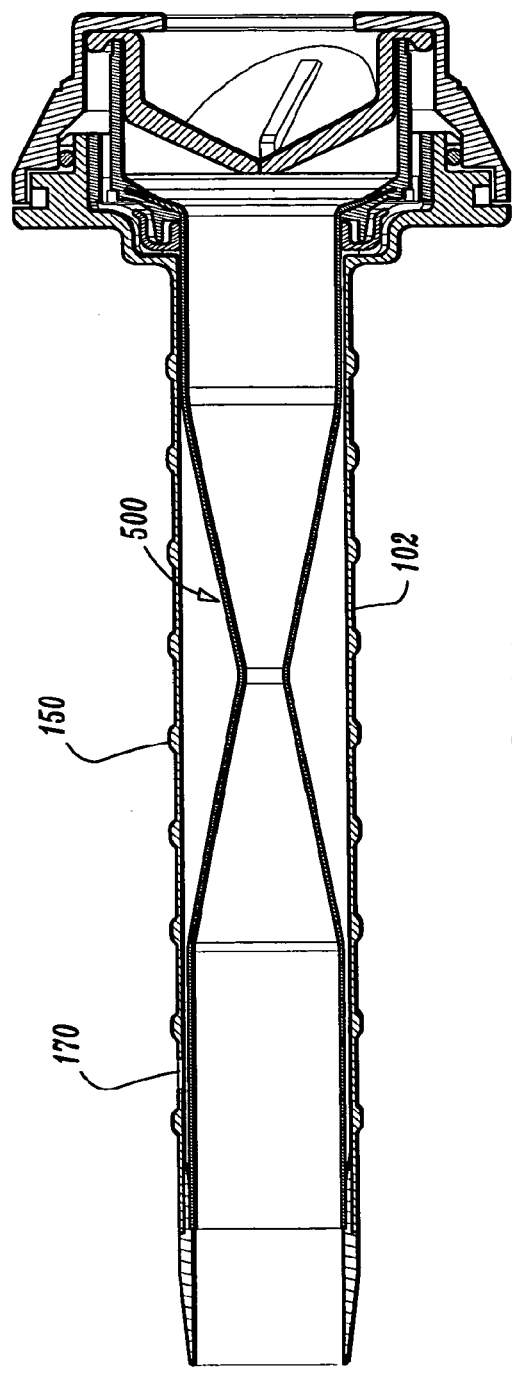
FIG. 15 is a side cross-sectional view of another embodiment of an access apparatus of the present disclosure.
Figure 16:
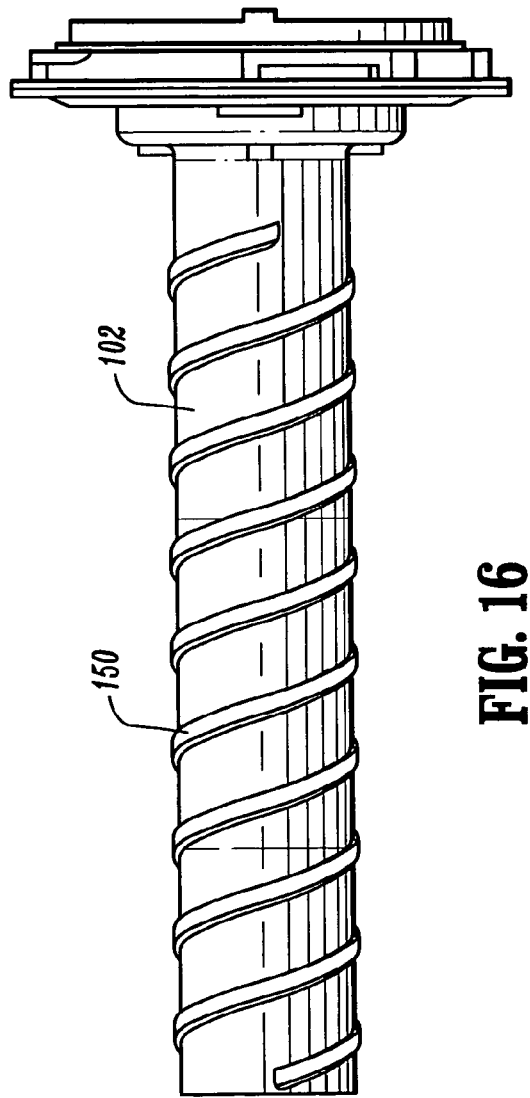
FIG. 16 is a side plan view of the access member of the access apparatus in accordance with the embodiment of FIG. 15.

FIGS. 15-16 illustrate a cannula assembly according to an alternate embodiment. Cannula sleeve 102 includes an external thread 150 formed on its outer surface. Thread 150 facilitates insertion of the cannula assembly 100 within the tissue site. Specifically, rotational movement of the cannula assembly 100 causes the thread 150 to engage the tissue and cause advancing movement within the body cavity. Thread 150 is shown as continuous; however, thread 150 could include partial interrupted thread segments and still be effective in advancing cannula assembly 100 within tissue.

Cannula sleeve 102 may also include an opening 170 in its outer surface. Opening 170 permits passage of insufflation gases between outer space (defined between the elongated seal 500 and cannula sleeve 102) and the abdominal cavity to either maintain insufflation within the body cavity and/or permit gases to enter or exit the outer space to equalize pressure of the outer space with the abdominal cavity and the internal passage of the elongated seal 504. In this embodiment, the elongated seal may be entirely impermeable to insufflation gases.

While the invention has been particularly shown, and described with reference to the preferred embodiments, it will be understood by those skilled in the art that various modifications and changes in form and detail may be made therein without departing from the scope and spirit of the invention. For example, persons of ordinary skill in the art may devise alternative means for mounting the slit seal or elongate seal, which would be contemplated herein. In addition, the slit seal may be omitted and the elongate seal may be arranged to block the passage through the cannula sleeve. In further embodiments, different means for introducing insufflation gases, such as a passageway incorporated in or secured to the cannula sleeve. In other embodiments, the braided or other fabric material is formed in a layer, and the ends of the layer are stitched together or otherwise joined together to form a tubular shape. In further embodiments, the elastomeric portion extends only over the upper portion of the fabric material. In further embodiments, the elastomeric material is omitted and the fabric material is relied upon to form a seal with instruments. Accordingly, modifications such as those suggested above, but not limited thereto, are to be considered within the scope of the invention.

What is claimed is:

1. A surgical access apparatus for providing access to the interior of the body, which comprises:
    a sleeve defining a longitudinal axis and having proximal and distal ends, the sleeve including an inner wall defining a longitudinal opening for passage of a surgical object;
    a seal member at least partially disposed within the inner wall of the sleeve, the seal member being generally elongated extending along the longitudinal axis of the sleeve, the seal member having an inner surface defining a seal passage and being adapted to form a substantial sealing relation with a surgical object; and
    a seal mount secured to the seal member and disposed adjacent the distal end of the sleeve, the seal mount mounted for longitudinal movement relative to the sleeve to accommodate passage of the surgical object through the seal passage of the seal member,
    the seal member being elongated to define a proximal seal end and a distal seal end, the proximal seal end being secured within the sleeve and the distal seal end being secured to the seal mount,
    the seal mount being dimensioned and adapted to move in a general proximal longitudinal direction upon insertion of the surgical object through the passage of the seal member to facilitate displacement of the inner surface of the seal member and alter a size of the seal passage.

2. The access apparatus according to claim 1 wherein the seal mount is at least partially disposed within the sleeve.

3. The access apparatus according to claim 1 wherein the seal member is mounted within the sleeve to define an outer passageway between the sleeve and the seal member.

4. The access apparatus according to claim 1 wherein the access apparatus includes a cannula housing at a proximal end thereof and the sleeve extends distally from the cannula housing.

5. The access apparatus according to claim 4 wherein the cannula sleeve includes a seal support disposed therein and wherein the seal member is secured within the cannula sleeve via the seal support.

6. The access apparatus according to claim 4 wherein the cannula housing includes a zero closure valve adapted to substantially close in the absence of the surgical object.

7. The access apparatus according to claim 1 wherein the seal mount has a configuration that includes a key depending therefrom and the inner wall of the sleeve includes a recess defining, in the inner wall of the sleeve a proximal key stop member and a distal key stop member, the key being accommodated within the recess and dimensioned to traverse the recess during longitudinal movement of the seal mount with respect to the sleeve such that the seal mount retains the configuration during traversal of the key in the recess between the proximal and distal stop members during longitudinal movement of the seal mount with respect to the sleeve.

8. A surgical access apparatus for providing access to the interior of the body, which comprises:
    a sleeve defining a longitudinal axis and having proximal and distal ends, the sleeve including an inner wall defining a longitudinal opening for passage of a surgical object;
    a seal member at least partially disposed within the inner wall of the sleeve, the seal member being generally elongated extending along the longitudinal axis of the sleeve, the seal member having an inner surface defining a seal passage and being adapted to form a substantial sealing relation with a surgical object; and
    a seal mount secured to the seal member and disposed adjacent the distal end of the sleeve, the seal mount mounted for longitudinal movement relative to the sleeve to accommodate passage of the surgical object through the seal passage of the seal member,
    wherein the seal member comprises a fabric material and an elastomeric material.

9. The access apparatus according to claim 8 wherein the fabric material of the seal member comprises a tubular braided fabric material.

10. The access apparatus according to claim 8 wherein the seal member is substantially impervious to passage of insufflation gases along a substantial length of the seal member.

11. The access apparatus according to claim 8 wherein the seal mount has a configuration that includes a key depending therefrom and the inner wall of the sleeve includes a recess defining, in the inner wall of the sleeve a proximal key stop member and a distal key stop member, the key being accommodated within the recess and dimensioned to traverse the recess during longitudinal movement of the seal mount with respect to the sleeve such that the seal mount retains the configuration during traversal of the key in the recess between the proximal and distal stop members during longitudinal movement of the seal mount with respect to the sleeve.

* * * * *